United States Patent [19]

Rossini et al.

[11] Patent Number: 4,489,059

[45] Date of Patent: Dec. 18, 1984

[54] ANOREXIGENIC COMPOSITION AND METHOD

[76] Inventors: Aldo A. Rossini, 62 Rambling Rd., Sudbury, Mass. 01776; John P. Mordes, 80 Devonshire Rd., Waban, Mass. 02168; Susan E. Leeman, 139 Park St., Newton Corner, Mass. 02158; Robert E. Carraway, 17 Brentwood Dr., Holden, Mass. 01520; Susan E. Ruane, Greenacres, Medway, Mass. 02053

[21] Appl. No.: 497,629

[22] Filed: Jun. 21, 1983

Related U.S. Application Data

[63] Continuation of Ser. No. 375,876, May 7, 1982, abandoned.

[51] Int. Cl.³ .......................................... A61K 35/407
[52] U.S. Cl. ...................................... 424/106; 424/95; 424/177
[58] Field of Search .......................... 424/95, 106, 177

[56] References Cited

PUBLICATIONS

Chemical Abst.–10th Collect. Index vol. 86–95 (1977–1981) p. 13,682 GS.

*Primary Examiner*—Sam Rosen
*Attorney, Agent, or Firm*—William B. Walker

[57] ABSTRACT

A water-soluble aqueous extract obtained from a 5123 Morris Hepatoma contains an anorexigenic agent having a molecular weight of from 3500 to 10,000 Daltons.

9 Claims, 1 Drawing Figure

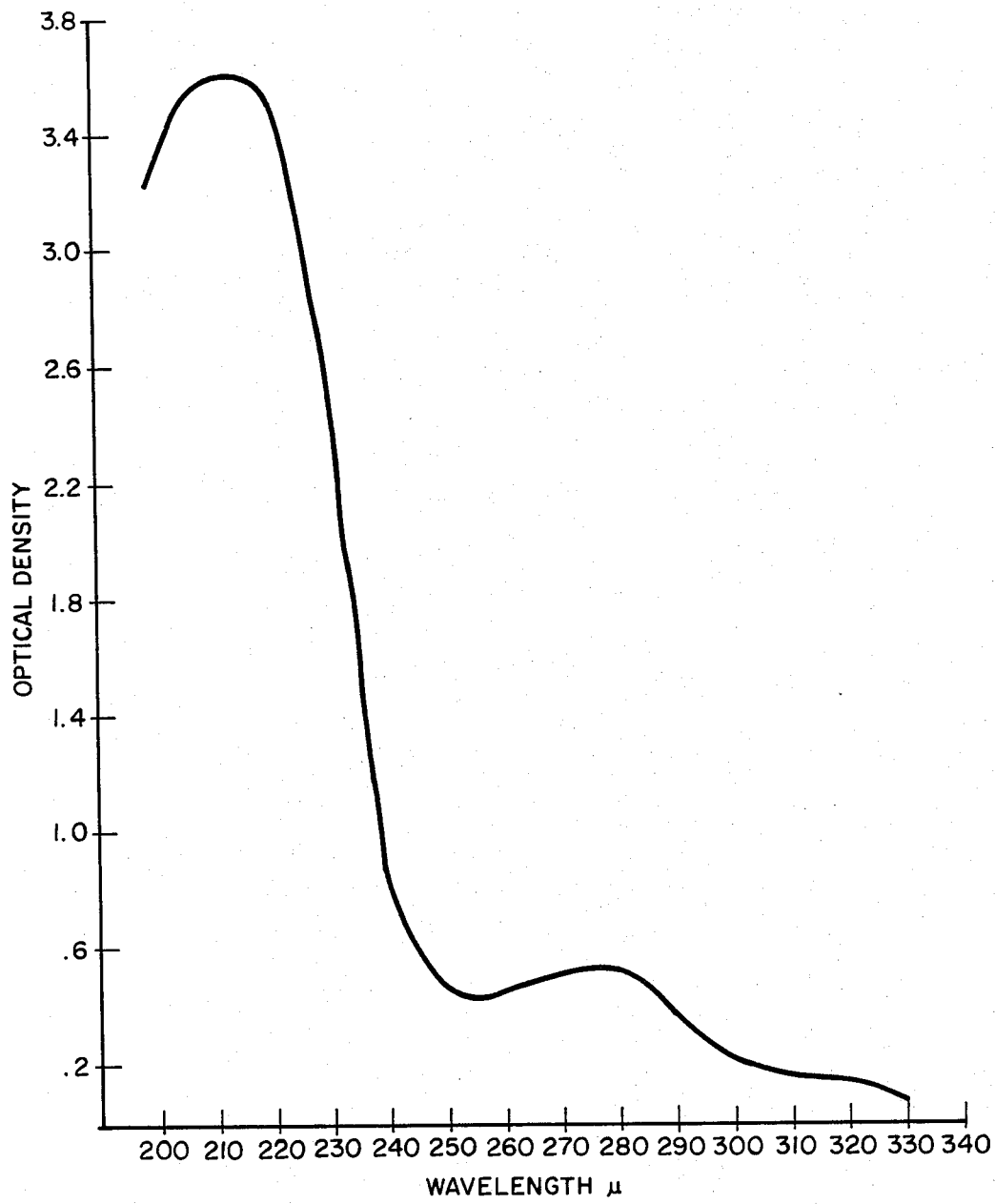
Fig_1

ANOREXIGENIC COMPOSITION AND METHOD

The Government has rights in this invention pursuant to Grant No. 117-82 awarded by the Department of Health and Human Services.

This application is a continuation, of application Ser. No. 375,876, filed May 7, 1982, now abandoned.

Field of the Invention

This invention relates to a novel anorexigenic composition and methods for its use and manufacture. The composition is a purified extract of a 5123 Morris Hepatoma.

Background of the Invention

Description of the Prior Art

Pharmacologic agents have been previously used to induce anorexia. The agents most commonly used are the amphetamines including dextroamphetamine, benzphetamine, diethylpropion and phenmetrazine. These compounds are indirectly acting sympathomimetic agents, effecting release of norepinephrine, causing a wide variety of peripheral side effects and always risking drug dependency. There are generally no anorectic agents currently available for treatment of obesity which are generally regarded as both efficacious and safe.

The presenting sympton of cancer is often decreased appetite and weight loss. The weight loss cannot be accounted for by the tumor burden. It has been suggested that tumor induced anorexia may represent a paraneoplastic syndrome mediated by a circulating substance by A. Theologides, "Anorexia-producing Intermediary Metabolite", J. Clin. Nutr. 29, 552–558 (1976) and W. D. Odell et al, "Humoral Syndrones Associated with Cancer," Ann. Rev. Med. 29, 379–406 (1978). However, such a theory has not been heretofor substantiated.

U.S. Pat. application Ser. No. 375,877 filed concurrently herewith entitled "Anorexigenic composition and Method" by John P. Mordes and Aldo A. Rossini discloses that a water-soluble, polar solvent extract obtained from a 5123 Morris Hepatoma has high anorexigenic activity.

SUMMARY OF THE INVENTION

The anorexigenic agent of this invention is originally derived from a 5123 Morris Hepatoma, exhibits anorexigenic activity in mammals and is characterized by the following properties:
(a) it has a molecular weight within the range of 3500 to 10,000 Daltons,
(b) it is deactivated by peptidase,
(c) it is stable in aqueous solution at pH 4.5 heated at 100° C. for 10 minutes.
(d) it is strongly bound by cation exchange resins,
(e) it is not absorbed by a hydrophobic chromatographic resin,
(f) it precipitates from aqueous solution at pH 7, and
(g) it has the spectrophotometric spectrum shown in FIG. 1 when in the form of a purified concentrate derived from the 5123 Morris Hepatoma.

The method of this invention for reducing appetite in mammals comprises administering an appetite suppressing amount of the above-characterized anorexigenic agent. The process for deriving the anorexigenic agent of this invention from a 5123 Morris Hepatoma and compositions containing the agent are also part of this invention.

The process of this invention for preparing a purified concentrate of the anorexigenic agent of this invention comprises:
(a) extracting an acidic aqueous homogenate of a 5123 Morris Hepatoma with a non-polar, lipophilic solvent, separating the aqueous phase, and removing the solvent from the aqueous phase to yield an initial residue, and
(b) purifying the initial residue by applying an aqueous extract of the initial residue acidified to a pH of 1.5 to 5.0 to a hydrophilic gel column and eluting the column with water acidified to a pH from 1.5 to 5.0, and
(c) collecting the eluate corresponding to the first fractions corresponding to an optical density peak at a wavelength of 280 $\mu$ greater than 1.6, and removing the solvent therefore to form a second residue.

Preferably, the procedure of step (b) is repeated and cation exchange resin chromatography is employed to yield a purified concentrate.

Brief Description of the Drawings

FIG. 1 is a spectrophotometric spectrum of the purified concentrate of this invention.

Detailed Description of the Invention

The anorexigenic agent of this invention is obtained from the 5123 Morris Hepatoma which is available from the tumor bank maintained by the Mason Research Institute, 57 Union Street, Worcester, Me. 01608. This is a tumor which can be serially transplanted in Buffalo rats. The tumor is preferably harvested when about 2 cm by 5 cm in size. The tumors are immediately immersed in liquid nitrogen following removal from the rats and are stored at −40° C. until they are processed.

The tumors are first homogenized by standard procedures for disrupting cellular tissue. For example, they can be homogenized in dilute cold aqueous hydrochloric acid solution and then further homogenized after adding acetone. The solids are removed by centrifugation yielding an aqueous solution or dispersion. The latter is extracted with a lipophilic non-polar solvent to separate undesirable constituents from the aqueous phase, and the aqueous phase is separated and then preferably frozen and lyophilized.

The lyophilized residue can be treated to remove residual insoluble material by resuspending it in water, centrifuging it, and lyophilizing the supernatant to yield an extract residue having anorexic activity.

Further purification to separate the active constituent from inactive components can be achieved by hydrophilic gel chromatography. Examples of suitable hydrophilic gels include the polydextran gels such as SEPHADEX (sold by Pharmacia, Uppsala, Sweden), polyacrylamide gels such as BIO-GEL (Prepared by Bio-RAD Laboratories, Richmond, Calif. and the agarose or agar gels such as SEPHAROSE (Pharmacia). An aqueous extract of the extract residue is acidified to a pH of 1.5 to 5.0 and preferably from 2 to 3. The acidified extract is applied to the gel column and eluted with water acidified to a pH of 1.5 to 5.0, preferably from 2 to 3. The acidifying agent is preferably a water-soluble aliphatic agent such as acetic acid.

The eluate fractions are collected, and the active fractions identified by examination for optical density at a frequency of 280 μ using a standard spectrophotometer such as a Guilford Spectrophotometer (Model 240). The first fractions having an optical density of 1.6 or greater are separated and pooled. The optical density of fractions subsequently obtained will fall below this level, and nothing thereafter should be retained.

The active fractions are then cooled and the solvent is removed, for example by lyophilization, to yield an active concentrate.

This concentrate can be still further purified by repeating the gel chromatographic procedure and by cation exchange resin chromatography. In the later procedure, the concentrate is applied to the column in acid solution and is eluted with an aqueous alkaline hydroxide solution having a high pH (above 10).

This concentrate can be administered parenterally, orally using an enteric coating, sublingually, rectally or by other standard procedures. For parenteral administration, the active material is preferably dispersed at a concentration of from 100 to 300 mg per liter in an isotonic solution suitable for parenteral injection.

This invention is further illustrated by the following specific but non-limiting examples. Temperature is given in degrees Celsius. The examples are descriptions of actual experiments unless otherwise indicated.

EXAMPLE 1

The extraction procedure for the Morris Hepatoma was as follows. The tumor was harvested when the subcutaneous tumors in rats achieved a size of about 2 cm by 5 cm. The rats were killed in an atmosphere of 100% $CO_2$. The tumors were immediately extirpated and then immersed in liquid nitrogen. After freezing, the tumors were kept at $-40°$ C. unitl use.

The tumor was extracted in 250 gm lots. The frozen preweighed tumor was added to 500 ml of 0.5 N cold HCl and homogenized for 90 sec. Then 2 liters of acetone were added to the mixture and homogenized for an additional 120 sec. The resultant mixture was centrifuged at 2,000 rpm for 45 minutes. The supernatant was then extracted twice with 4 liters of petroleum ether. The aqueous phase was separated and reduced in volume to 1500 ml, frozen, and lyophilized.

EXAMPLE 2

For purification using gel filtration 8 lots of 250 mg of tumor were prepared. Approximately 100 g of initial lyophilized residue (5% yield) was obtained. This residue was resuspended in distilled water to a concentration of 0.2 gm/ml. This suspension was centrifuged at 10,000 rpm for 15 minutes. The supernatant pH was then adjusted to 2.5 with 8 M NaOH and recentrifuged at 10,000 rpm for 15 min. The supernatant was then applied to an 18 liter SEPHADEX G-25 column run with 0.2 M acetic acid, pH 2.5. 35 Fractions of 500 ml each were collected and stored at 5° C.

Seven pools were tested for bioactivity.

| Pool | Fractions |
|------|-----------|
| 1 | 1–5 |
| 2 | 6–10 |
| 3 | 11–15 |
| 4 | 16–20 |
| 5 | 21–25 |
| 6 | 26–30 |

-continued

| Pool | Fractions |
|------|-----------|
| 7 | 31–35 |

EXAMPLE 3

The residue obtained in Example 1 was tested in a bioassay system which was established as follows. Twentyfour rats housed individual metal hanging cages on a rack were kept in a small windowless room. The light cycle was reversed, such that the rats experienced darkness from 9 a.m. to 9 p.m. Since rats are nocturnal feeders, this arrangement allowed study of the rats during their usual feeding period. The rats were allowed water continuously ad libitum, but were given food (a balanced Purina rat chow in powder form) only from 9 a.m. to noon. The food was in 16 oz glass jars with a 3 cm opening in the lid to minimize spillage. This arrangement allowed for rapid determination of food intake by weighing the jars. Within a week of being placed on a 3-hours-a-day of food regimen, most 200 g rats stabilized at a food intake of 12 to 16 gm food per 3 hour feeding period. They maintained their weight on this regimen, but did not grow. This sensitive bioassay system thus permitted the detection of small but significant anorectic activity, for it tested food consumption in rats fasted for 21 hours and trained to eat voraciously when offered food.

The anorectic activity of the crude extract was determined in the bioassay as follows. In all experiments described hereafter, Day "O" refers to the day on which the injection was administered. Days $-1$ and $+1$ are the preceeding and following days, respectively. All data refer to gram of food eaten during the 3 hours of feeding. The following are the results obtained.

|  |  | DAYS | | |
|---|---|---|---|---|
|  |  | −1 | 0 | +1 |
| GROUP I (a) | N = 4 | 10.9 ± 1.1 | 5.2 ± 2.6 | 5.8 ± 0.7 |
| GROUP II (b) | N = 4 | 10.8 ± 1.1 | 9.2 ± 0.5 | 6.6 ± 0.2 |
| GROUP III (c) | N = 3 | 11.2 ± 0.6 | 11.0 ± 5.7 | 6.3 ± 1.2 |

(a) 105 mg crude extract/rat, 3 cc, pH 7.0, 463 mOsm/kg
(b) 50 mg crude extract/rat, 3 cc, pH 7.0, 284 mOsm/kg
(c) 3 cc normal saline/rat, pH 7.0, 300 mOsm/kg (control)

From these data it can be concluded that anorexigenic bioactivity was present in the extract of Morris Hepatoma. Further, since the extracted material was soluble in 75% acetone, it can also be concluded that the molecular weight of the extracted anorexigenic material is likely to be less than approximately 10,000 Daltons.

EXAMPLE 4

Repeating the procedure of Example 3 with residue of the purified fractions obtained in Example 2, the results shown in the following table were obtained:

| Pool | pH | mOsm/kg | N | −1 | 0 | +1 |
|------|------|---------|---|------|------|------|
| 1 | 4.90 | 232 | 5 | 12.7 ± 2.3 | 1.2 ± 0.8 | 5.8 ± 1.4 |
| 2 | 5.40 | 267 | 4 | 13.2 ± 1.7 | 7.1 ± 1.3 | 10.7 ± 1.2 |
| 3 | 5.65 | 272 | 4 | 13.8 ± 2.9 | 6.9 ± 3.0 | 9.3 ± 1.9 |
| 4 | 4.98 | 360 | 4 | 10.7 ± 1.2 | 6.4 ± 1.3 | 9.2 ± 1.5 |
| 5 | 5.11 | 325 | 5 | 8.9 ± 2.0 | 8.1 ± 1.1 | 8.7 ± 1.6 |
| 6 | 5.66 | 349 | 5 | 12.8 ± 2.0 | 10.7 ± 0.6 | 8.9 ± 2.0 |
| 7 | 5.14 | 287 | 4 | 9.3 ± 1.9 | 9.6 ± 1.2 | 9.1 ± 1.2 |
| Sa- | 4.94 | 278 | 4 | 13.5 ± 1.2 | 8.8 ± 1.6 | 9.3 ± 1.4 |

| Pool | pH | mOsm/kg | N | −1 | 0 | +1 |
|------|------|---------|---|------------|------------|------------|
| Saline | 5.02 | — | 4 | 9.3 ± 1.4 | 10.9 ± 1.9 | 10.0 ± 0.5 |

From these data it can be seen that anorexigenic activity as measured in the bioassay system is very high and is far greatest in the first pool of fractions. This pool had an optical density greater than 1.6 measured at a frequency of 280 μ, indicating a distinct, early protein peak.

EXAMPLE 5

The residue obtained by lyophilizing the solution of Pool 1 in Example 2 was resuspended in 0.2 M acetic acid buffer (pH 2.5). This aqueous solution was applied to a 2.2 L chromatography column containing Sephadex G-75 gel. The column was eluted with 0.2 M acetic acid, pH 2.5 and 75 fractions of 25 ml each were collected. Aliquots of 10 ml were taken from each fraction and pooled as follows:

| Pool 8 | 10 cc each from fractions 1 to 25 |
|--------|-----------------------------------|
| Pool 9 | 10 cc each from fractions 26 to 50 |
| Pool 10 | 10 cc each from fractions 51 to 75 |

When tested at appropriate dilution in the previously described bioassay system, anorectic activity was observed in Pools 8, 9 and 10.

| Injection | pH | N | −1 | 0 | +1 |
|-----------|------|---|-------------|------------|-----------|
| Pool 8 | 4.99 | 4 | 12.5 ± 4.05 | 1.2 ± 0.9 | 5.9 ± 0.9 |
| Pool 9 | 4.99 | 4 | 12.7 ± 3.9 | 2.2 ± 0.8 | 8.3 ± 1.7 |
| Pool 10 | 4.99 | 4 | 12.4 ± 2.8 | 2.1 ± 3.9 | 7.3 ± 1.8 |
| Saline | 5.00 | 4 | 12.1 ± 2.0 | 10.7 ± 1.9 | 10.2 ± 1.3 |

EXAMPLE 6

Pools 8 and 9 of Example 5 were lyophilized, and the residue was suspended in 0.2 M acetic acid. This material at pH 2.5 was again applied to a 2.2 L chromatography column containing Sephadex G-75 gel. The column was eluted with 0.2 M acetic acid, and 75 fractions were again collected. Again aliquots of 10 cc were used to form 3 pools. When tested in bioassay, activity was now found confined to Pool 12.

| Injection | N | pH | −1 | 0 |
|-----------|---|------|------------|------------|
| Pool 11 | 5 | 5.0 | 15.4 ± 2.1 | 11.3 ± 4.1 |
| Pool 12 | 5 | 5.0 | 14.9 ± 1.5 | 7.3 ± 2.5 |
| Pool 13 | 5 | 5.0 | 14.9 ± 1.6 | 13.2 ± 1.8 |
| Saline | 4 | 5.0 | 15.0 ± 1.7 | 14.5 ± 1.3 |

EXAMPLE 7

The remainder of bioactive Pool 12 in Example 6 was subjected to proteolytic digestion according to the following protocol. A volume equivalent to 7.5 doses (a dose is the amount required to effect a 50% reduction in food intake) was lyophilized and resuspended in distilled water at pH 2.5. This was divided into two equal portions. To one portion 30 mg of pepsin was added. Both solutions were then incubated at 40° for 24 hrs. Then the pH of both flasks was raised to 7.0, and 30 mg of pancreatic protease was added to the pepsin containing portion. Both were reincubated at 40° for 17 hrs. The pH of both was then lowered to 4.5 with 1N HCL. A third flask containing 30 mg pepsin and 30 mg pancreatic protease in saline at pH 5 was also made up. All three samples were then boiled for 10 minutes and then coassayed.

| Injection | pH | N | osmolality | −1 | 0 |
|-----------|------|---|------------|------------|------------|
| Material without enzyme treatment | 4.99 | 4 | 110 | 15.0 ± 1.8 | 4.1 ± 1.3 |
| Material treated with enzymes | 5.01 | 4 | 132 | 14.9 ± 1.7 | 8.8 ± 2.2 |
| Solution of enzymes alone | 4.99 | 4 | 250 | 14.9 ± 1.3 | 9.8 ± 0.8 |
| Saline | 5.00 | 5 | 285 | 14.3 ± 1.9 | 14.1 ± 1.7 |

From these results it can be concluded:

(1) that the anorectic activity obtained from G-25 and then G-75 chromatography of hepatoma extract is destroyed by peptidase treatment, and (2) this same activity is stable when boiled for 10 minutes at pH 5.

EXAMPLE 8

Further studies were performed on the biologically active Pool 10 obtained in Example 5. A volume equivalent to approximately 75 doses was applied to a hydrophobic chromatographic resin column (Bondupak Sep-Pak C-18, Waters Associates, Inc., Milford, MA). This column was eluted with 2 ml methanol and 2 ml of 50% acetonitrile. Both the runthrough and the eluate of the Sep-Pak were tested for activity. Both were first lyophilized to remove solvents.

| Injection | N | pH | −1 | 0 |
|-----------|---|------|------------|------------|
| Runthrough | 4 | 5.0 | 15.0 ± 0.9 | 0.8 ± 0.6 |
| Eluate | 5 | 5.0 | 10.9 ± 1.6 | 14.0 ± 2.5 |
| Saline | 4 | 5.0 | 15.2 ± 2.2 | 15.8 ± 2.4 |

Then results indicated that the anorectic activity does not adhere to a Bondupak Sep-Pak column under the conditions specified.

EXAMPLE 9

A spectrum of the material in Pool 10 obtained with a Model 240 Guilford Spectrophotometer (Guilford Instruments, Obertin, Ohio). This spectrum is shown in FIG. 1.

EXAMPLE 10

The standard ninhydrin reaction was performed on the same material used in Example 9. Ninhydrin (10%) in acetone and 3% Cadmium acetate were used. The protein concentration estimate was 1 mg/ml. Since a dose was found to be 4 ml, the dose of crude G-75 extract is 4 mg/dose.

EXAMPLE 11

Ten doses of material from Pool 10 obtained in Example 5 were lyophilized and then resuspended in 0.2 N acetic acid. Five doses were brought to pH 5.08. Five doses were brought to pH 7.01 at which time a precipitate formed. This sample was then immediately spun at 12,000 r.p.m. for 10 minutes. The supernatant was decanted. The pellet was resuspended in saline at pH 5.15. All solutions were assayed.

| Sample | pH | N | -1 | 0 |
|---|---|---|---|---|
| A | 5.08 | 5 | 10.7 ± 1.9 | 8.1 ± 1.6 |
| B | 5.03 | 5 | 10.9 ± 1.7 | 9.4 ± 0.6 |
| C | 7.18 | 5 | 11.7 ± 1.5 | 13.1 ± 1.8 |
| D | 5.15 | 5 | 11.8 ± 2.9 | 13.8 ± 1.6 |

A = Original active material
B = Material precipitated at pH 7, then redissolved
C = Decanted supernatant
D = Saline These data indicated that the anorectic activity is insoluble at pH 7.0, but may be recovered by rapid readjustment of pH to 5.0.

EXAMPLE 12

Material from Pool 10 obtained in Example 5 was applied in 4 different volumes to an SDS agarose gel (15% standard Laemli SDS gel system) using standard techniques. Comparison of the distribution in the lanes to which the samples were applied against lanes to which appropriate molecular weight markers had been applied showed all proteins present in the samples were of a molecular weight less than 25,000 Daltons.

EXAMPLE 13

Material from Pool 10 obtained in Example 5 was tested for stability at alkaline pH. Four doses were brought to pH 9 by slow addition of 0.1 and 1.0 N NaOH. A precipitate formed. Four doses were brought to pH 12 by rapid addition of 1 N NaOH. Both solutions were incubated at 5° overnight. The solution with the precipitate was centrifuged at 15,000 r.p.m. for 10 minutes. The supernatant was decanted and the pellet was resuspended with distilled $H_2O$ at pH 5.

| Sample | pH | osmolality | -1 | 0 |
|---|---|---|---|---|
| A | 6.04 | 247 | 13.0 ± 1.5 | 12.5 ± 2.5 |
| B | 5.18 | 179 | 12.9 ± 1.0 | 9.7 ± 1.1 |
| C | 5.12 | 370 | 12.9 ± 1.0 | 1.0 ± 1.0 |
| D | 5.0 | 285 | 12.9 ± 0.9 | 13.6 ± 1.5 |

A = Supernatant after incubation at pH 9
B = Pellet formed on incubation at pH 9
C = Incubation at pH 12
D = Saline These results indicate the activity is stable or enhanced on incubation at pH 12, but is diminished by incubation at pH 9.

EXAMPLE 14

Material from Pool 10, Example 5 (40 ml, 10 doses, pH 2.5) was applied to a 50 cc Sephadex SP-C25 Cation exchange resin chromatography column. The column was washed with 20 cc 0.2 N acetic acid, then eluted with 50 ml of 1 M pyridine acetate, pH 5.5, then eluted again with undiluted pyridine acetate, pH 5.5, and finally again eluted with 0.1 N HCl. No bioactivity could be recovered upon assay, indicating that the material is highly bound to SP Sephadex resin and is probably highly negatively charged.

EXAMPLE 15

The procedure of Example 14 was repeated. Material from Pool 10, Example 5 (80 ml, 20 doses, pH 3,75) was applied to a 50 cc Sephadex SP-C25 Cation exchange resin chromatography column. The column was washed with 20 cc of acetic acid pH 3.75, then eluted with 50 ml 1M $NH_4OH$, pH 11.7. Two 25 ml elution fractions were collected. The pH 3.75 washings and the two pH 11.7 fractions were adjusted to approximately pH 5.7 with 0.1 N HCl and tested.

| Sample | pH | osmolality | N | -1 | 0 | +1 |
|---|---|---|---|---|---|---|
| A | 5.86 | 370 | 4 | 16.0 ± 2.5 | 11.5 ± 3.0 | 7.6 ± 2.0 |
| B | 5.75 | 112 | 4 | 16.0 ± 2.2 | 12.6 ± 5.2 | 9.5 ± 1.8 |
| C | 5.57 | 169 | 4 | 16.0 ± 1.9 | 6.3 ± 2.4 | 10.1 ± 2.8 |
| D | 5.0 | 285 | 4 | 15.7 ± 1.4 | 12.5 ± 3.1 | 9.8 ± 2.4 |

A = Washings obtained with acetic acid pH 3.75
B = First elution fraction using $NH_4OH$ at pH 11.7
C = Second elution fraction using $NH_4OH$ at pH 11.7
D = Saline From these data it can be concluded that the activity is bound to Sephadex SP ion exchange resin and can be recovered by elution at high pH.

EXAMPLE 16

Material from Pool 10, Example 5 (25 ml, pH 2.5) was placed within a Spectraphor dialysis membrane tubing (Spectrum Medical Industries, Inc., Los Angeles, Calif.) having a pore size designed to exclude molecules of molecular weight greater than 3,500 Daltons. The material within the membrane was dialyzed against 2 L of 0.2 M acetic acid at pH 2.5 for 2 days. There were 2 changes of the dialysis solution. It was found that the bioactive material remained within the dialysis tubing.

| Injection | pH | OSM | N | -1 | 0 | +1 |
|---|---|---|---|---|---|---|
| Materials within dialysis membrane | 5.0 | 106 | 4 | 11.8 ± 1.2 | 6.9 ± 0.8 | 8.5 ± 1.0 |
| Saline | 5.8 | 295 | 4 | 11.6 ± 1.2 | 11.5 ± 1.2 | 11.6 ± 1.6 |

The invention claimed is:

1. An anorexigenic agent in purified form, characterized in that:
   (a) it is present in aqueous extracts of 5123 Morris Hepatoma,
   (b) it has a molecular weight within the range of 3500 to 10,000 Daltons,
   (c) it is deactivated by peptidase,
   (d) it is stable in aqueous solution at pH 4.5 heated at 100° C. for 10 minutes,
   (e) it is strongly bound by cation exchange resins,
   (f) it is not absorbed by a hydrophobic chromatographic resin,
   (g) it precipitates from aqueous solution at pH 7, and
   (h) it has the spectrophotometric spectrum shown in FIG. 1 when in the form of a purified concentrate derived from a 5123 Morris Hepatoma.

2. An anorexigenic composition comprising the agent of claim 1 and a pharmaceutically acceptable, non-toxic excipient.

3. A method for reducing appetite in a mammal comprising administering an appetite suppressing dose of the agent of claim 1.

4. A method for reducing appetite in a mammal comprising administering an appetite suppressing dose of the composition of claim 2.

5. The method of claim 4 comprising injecting an aqueous, isotonic solution of the agent.

6. A process for isolating the anorexigenic agent of claim 1 from a 5123 Morris Hepatoma comprising
   (a) extracting an acidic aqueous homogenate of 5123 Morris Hepatoma with a non-polar lipophilic solvent, separating the aqueous phase remaining to yield an initial residue,
   (b) purifying an aqueous solution extract of the initial residue by applying the aqueous extract acidified to a pH of from 1.5 to 5.0 to a hydrophilic gel column and eluting the column with water acidified to a pH of from 1.5 to 5.0, and
   (c) collecting the eluate corresponding to the first fractions having an optical density greater than 1.6 measured at a frequency of 280 $\mu$ and removing the solvent therefrom to yield an active concentrate.

7. The method of claim 6 wherein the aqueous extract and water in step (c) are acidified with acetic acid to a pH of from 2 to 3.

8. The method of claim 7 wherein the active concentrate is further purified by repeated hydrophilic gel column chromatography.

9. The method of claim 8 wherein the active concentrate is further purified by cation exchange resin chromatography.

* * * * *